United States Patent [19]

Steins

[11] Patent Number: 5,735,822

[45] Date of Patent: Apr. 7, 1998

[54] TETHER FOR ELONGATED MEMBERS

[76] Inventor: Robert W. Steins, 7770 Regents Rd., #258, San Diego, Calif. 92122

[21] Appl. No.: 615,492

[22] Filed: Mar. 12, 1996

[51] Int. Cl.$^6$ ........................................ A61M 5/32
[52] U.S. Cl. .................. 604/179; 604/174; 128/DIG. 26
[58] Field of Search ........................... 128/869, 876, 128/878, DIG. 26; 604/179, 180

[56] References Cited

U.S. PATENT DOCUMENTS

| | | | |
|---|---|---|---|
| 3,782,388 | 1/1974 | Page | 604/180 |
| 4,392,853 | 7/1983 | Muto | 604/180 X |
| 4,988,338 | 1/1991 | Taylor et al. | 604/180 |
| 5,306,256 | 4/1994 | Jose | 604/180 |

*Primary Examiner*—Sam Rimell
*Assistant Examiner*—Robert V. Racunas
*Attorney, Agent, or Firm*—Karl M. Steins

[57] ABSTRACT

An apparatus for tethering elongated members, such as cables, tubes and the like, to a human body, is disclosed. The tether is configurable to attach to various human appendages and includes an embodiment that is strong enough to support a heavy cable, such as a hospital ultrasound equipment cable. The tether can further accommodate various diameters of cables, tubes, cords and the like, including writing implements, and can be comprised of various alternative substances, including semi-rigid, soft and non-allergenic materials. A critical aspect of the present invention is that the cable, tube, cord and the like be quickly releasable from the body by tugging the cable, tube, cord and the like.

15 Claims, 7 Drawing Sheets

TETHER FOR ELONGATED MEMBERS

BACKGROUND OF THE INVENTION

1. Field of the Invention

This invention relates generally to tethers for elongated members and, more specifically, to means for holding cords, tubes, cables and the like to a human body.

2. Description of Related Art

There are three areas that are generally related to the present invention. One related area is that of hospital ultrasound equipment. Diagnostic ultrasound equipment is in use in virtually every hospital in the United States, if not the world. The typical diagnostic ultrasound equipment comprises, generally, a base unit, a transducer array, and a multi-element cable connecting the two. In operation, the base unit controls the transducer array by transmitting electrical impulses to it via the cable. The transducer array converts these electrical impulses into ultrasonic waves that are directed into a human patient when the transducer array is held against the patient's body. These ultrasonic waves reflect off of soft tissues within the patient and are then received by the transducer array. The transducer array converts the received waves into electrical impulses that are transmitted via the cable back to the base unit for display and manipulation. In operation, therefore, the operator must stretch the cable from the base unit to the patient so that the transducer array can be placed on the patient's body.

New developments of hospital ultrasound equipment have sought to improve image resolution; this has been accomplished by adding channels, or individual dielectric elements, to the transducer array. Since each individual dielectric element requires its own cable element, increasing the transducer array size has increased the number of elements in the cable. Current cables comprise up to 700 individual elements. As elements were added, the cable weight has increased to the point that it now interferes with the handling and operation of the ultrasound equipment.

Figures 1A, 1B:
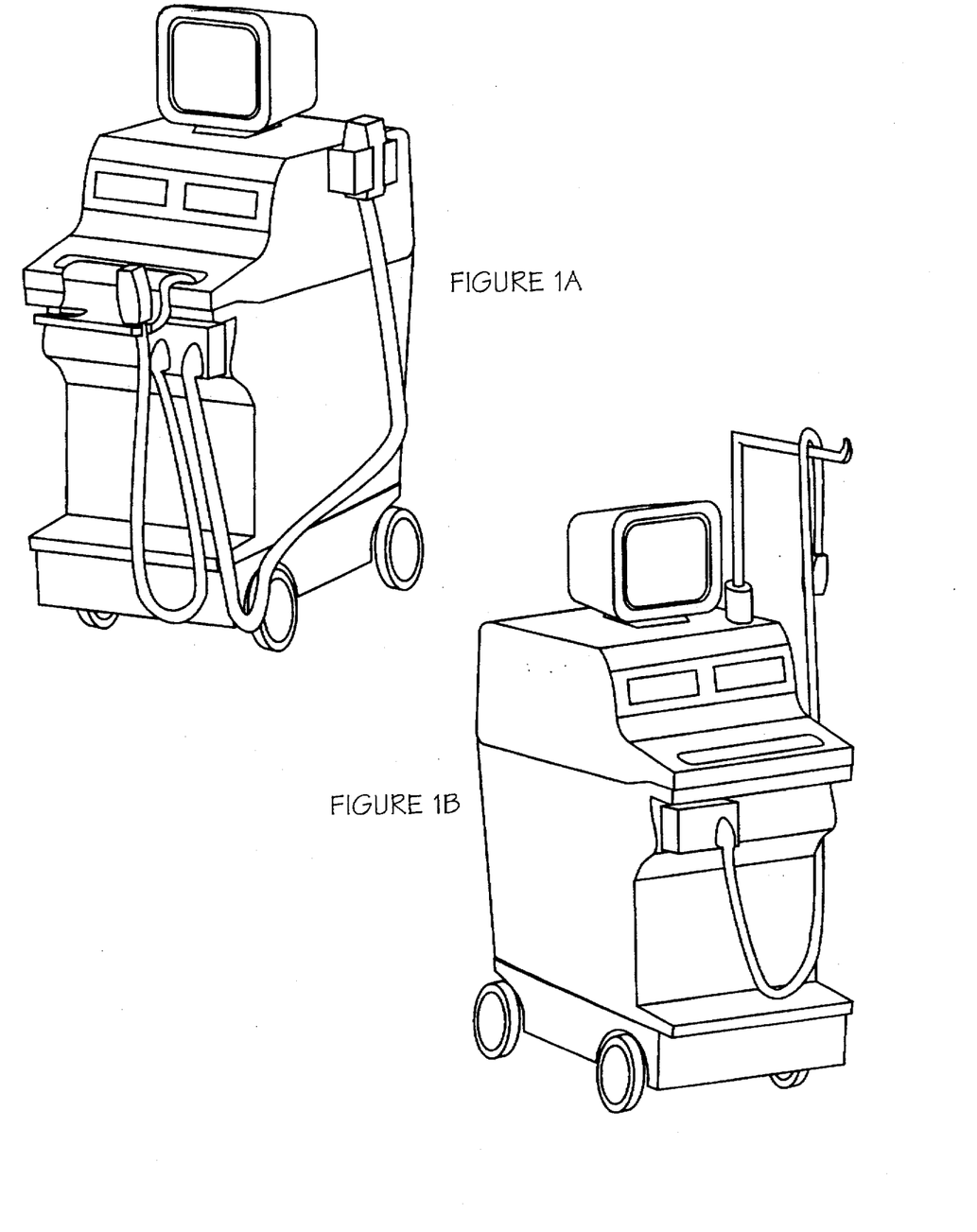
FIGS. 1a, 1b and 1c are perspective views of various prior art embodiments of ultrasound cable management devices.

These heavy cables become particularly unwieldy where the patient is located several feet from the base unit, such as in an operating room. The prior art cable management device such as the hook shown in FIG. 1a is not effective in such a situation because the operator is too far from the base unit to hang the cable from the hook when "scanning." Additionally, the operating room must be kept sterile. When a technician is required to move back and forth between the base unit and the patient in order to retrieve the transducer array, the sterile environment around the patient is in danger of compromise.

Figure 1C:
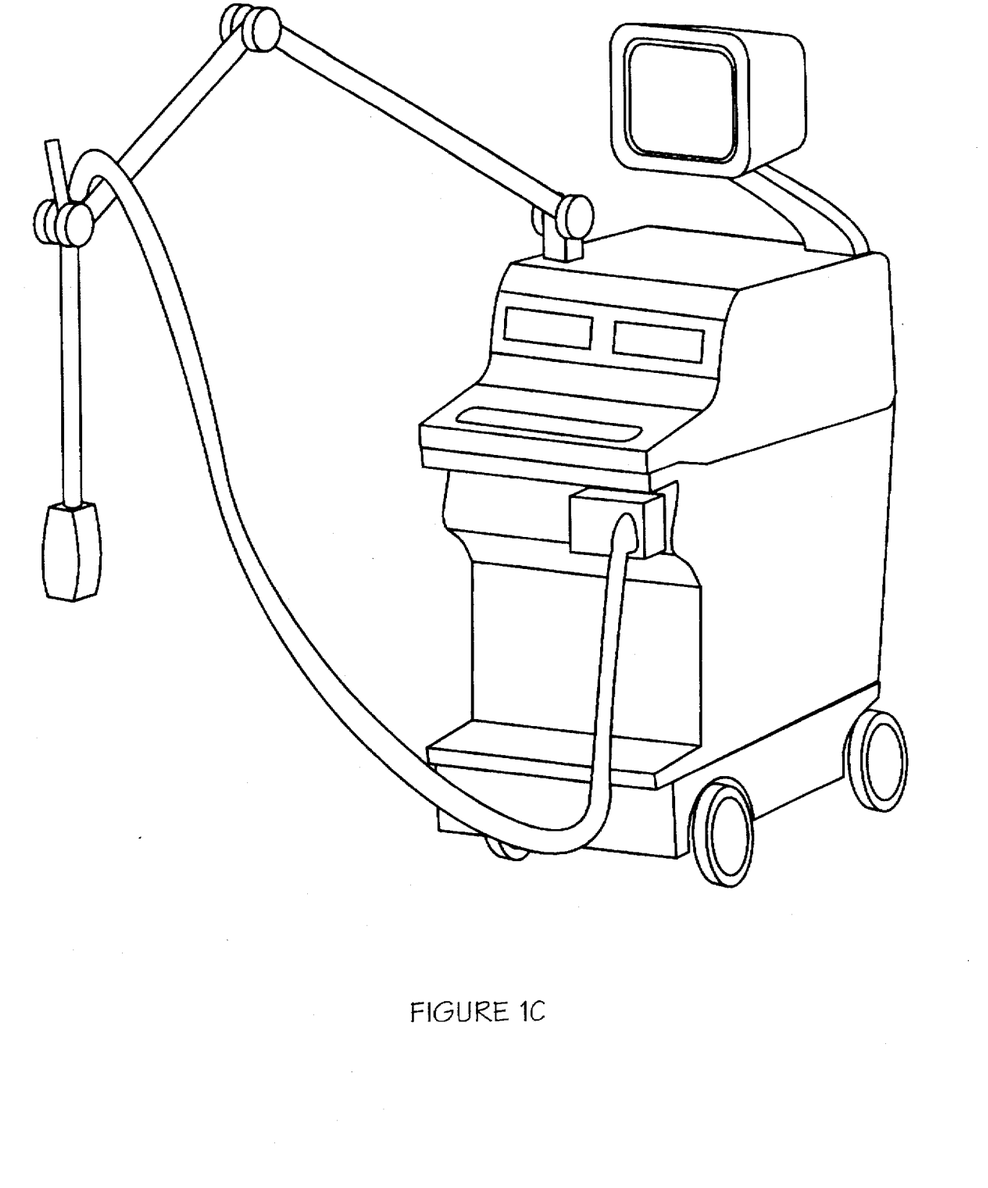

Similarly, the prior art cable management devices such as the overhead arms shown in FIGS. 1b and 1c are not effective because there is insufficient leverage at the base unit to permit the overhead arms to be long enough to reach the distant patient. Furthermore, these overhead arms have a tendency of interfering with patient movement and transducer array positioning.

Additionally, an operator frequently needs specialized marking pens and the like close at hand when he is performing a "scan." None of the prior art devices have a provision for holding a pen, etc. in the vicinity of the transducer array.

Another area related to the present invention is the management of the various tubes, electrical leads and monitoring cables that may be attached to a hospital patient. A patient in a hospital intensive care unit may, at any one time, have more than one intravenous (IV) tube, as well as cables and leads to several pieces of monitoring equipment running to and from his body.

Prior means of managing these tubes, cables and leads have included taping them to the patient's body with adhesive tape, clipping them to the patient's gown, or simply draping them over the patient (i.e. not attaching them to the patient at all).

There are drawbacks to all of these means. The patient may be allergic to adhesive tape; the tube, etc. could become detached from the patient when the patient moves or is moved; the hospital gowns are too loose to hold items clipped to them in one place—the lead or cable is allowed to slide across the patient's body, making it difficult to find when desired.

Another drawback of these prior methods involves the identification of the various tubes, etc. connected to the patient's body. These tubes, etc. can get tangled with each other over time, making it difficult for health care personnel to identify which tube, etc. comes from what source. The ability to hold these tubes, etc. in one place on the patient's body and also provide a means for labeling each tube, etc. would be helpful in this regard. It would also be beneficial to include the ability to hold varying sizes of tubes, leads, cables and the like.

A third area related to the present invention is that of electrical hand tools, such as electric hedge trimmers, electric saws, vacuum cleaners, hair dryers and the like, and their electrical cords. When using these tools at a distance from the electrical outlet, such as is the case when doing yard work, long lengths of electrical cord are necessary to supply electrical power. Current users of such tools must manually tend the cord, such as by throwing the cord over their shoulder or around their waist. Manually tending these cords can create a significant hazard of cutting the cord with the power tool. An additional problem lies in the distraction to the tool user that is created by the loose electrical cord; such a situation is dangerous, particularly if the power tool has a cutting portion. An untended cord can also present a tripping hazard. A method of maintaining slack in the electrical cord at the tool end and pulling the cord along with the user as he traverses an area, such as a yard, would be helpful.

OBJECTS AND SUMMARY OF THE INVENTION

In light of the aforementioned problems associated with the prior art, it is an object of the present invention to provide a means for managing a cable, tube, cord and the like by tethering it to a human body;

It is a second object of this invention that the tether be configurable to attach to various human appendages;

It is an additional object that it be strong enough to support a heavy cable, such as at least a 700-element hospital ultrasound equipment cable;

It is a further object of this invention that the tether accommodate various diameters of cables, tubes, cords and the like;

It is a further object of this invention that the tether be comprised of various alternative substances, including rigid, semi-rigid, soft and non-allergenic materials;

It is a further object of this invention that the tether be configured to hold writing implements and the like; and It is a further object of this invention that the cable, tube, cord and the like be quickly releasable from the body by tugging the cable, tube, cord and the like.

BRIEF DESCRIPTION OF THE DRAWINGS

The objects and features of the present invention, which are believed to be novel, are set forth with particularity in the

3 appended claims. The present invention, both as to its organization and manner of operation, together with further objects and advantages, may best be understood by reference to the following description, taken in connection with the accompanying drawings, of which:

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a tether for elongated members.

Figure 2:
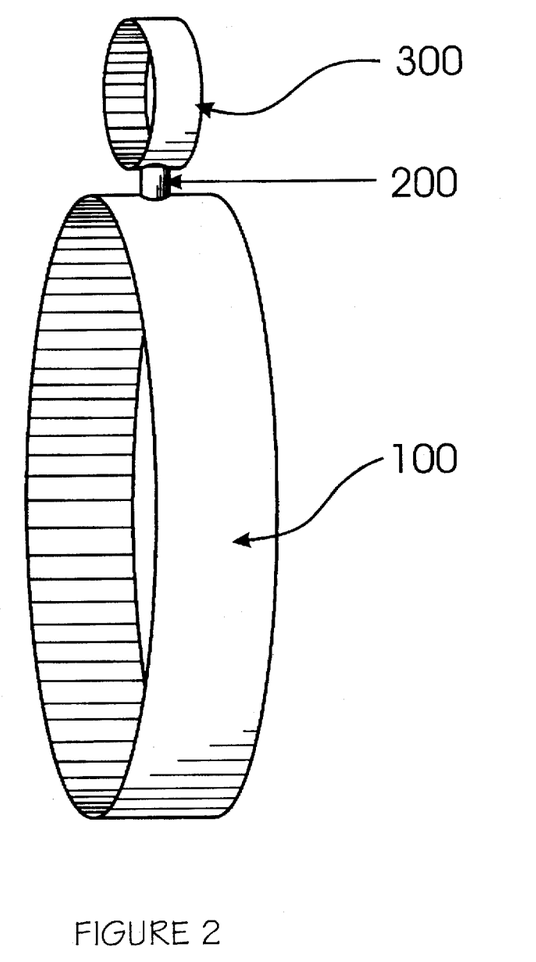
FIG. 2 is a perspective view of a preferred embodiment of the present invention showing the general arrangement of elements.

The tether 10 of the present invention can be best understood by initial consideration of FIG. 2. The tether comprises a strap 100, a clamp 300, and a connecting means 200 connecting the two. FIG. 2 is a perspective view of a preferred embodiment of the present invention showing the general arrangement of elements.

The strap 100 is depicted in a generic way in FIG. 2. In the preferred embodiment, the strap 100 will be comprised of a flexible material, such as a type of cloth webbing or pliable plastic, that will wrap around or slip over an appendage of the body of an intended user. The strap 100 could also be constructed of a rigid or semi-rigid material such as plastic; this would provide a more rigid platform to which the clamp can be attached. The strap 100 could be provided in various colors and textures, depending upon the intended application.

The strap 100 may be configured to accept a sheath over its entirety. This sheath could comprise a disposable material, such as plastic, such that the sheath could be replaced periodically in order to maintain sanitary conditions, for example.

Ideally, the strap 100 will be configured to grip several different sizes of appendage, including legs, arms, neck, or the waist. In it's preferred form, the strap 100 will also include a releasable closure means, such as "Velcro" or snaps, so that the user can automatically release himself from the tube, cord, or cable by pulling away from the tube, etc. (i.e. by exerting a force distal to the appendage), such as in an emergency. The materials used for construction and the designed resistance of the closure means to releasing of the strap 100 will depend upon the expected weight of the cable, etc. to be tethered. Tethers designed to tend a heavy cable, etc. will include the retaining strength to handle these cables.

The strap 100 further may include a display portion for inscribing indicia thereon, such as the equipment manufacturer's name or logo, or a patient's or owner's identity. The display portion could be configured to accept erasable or permanent inscriptions.

FIG. 2 further shows a generic representation of the connecting means 200. The connecting means 200 can comprise various forms, depending upon the particular application of the tether. Several of these embodiments are described below by reference to the subsequent figures.

Figure 3:
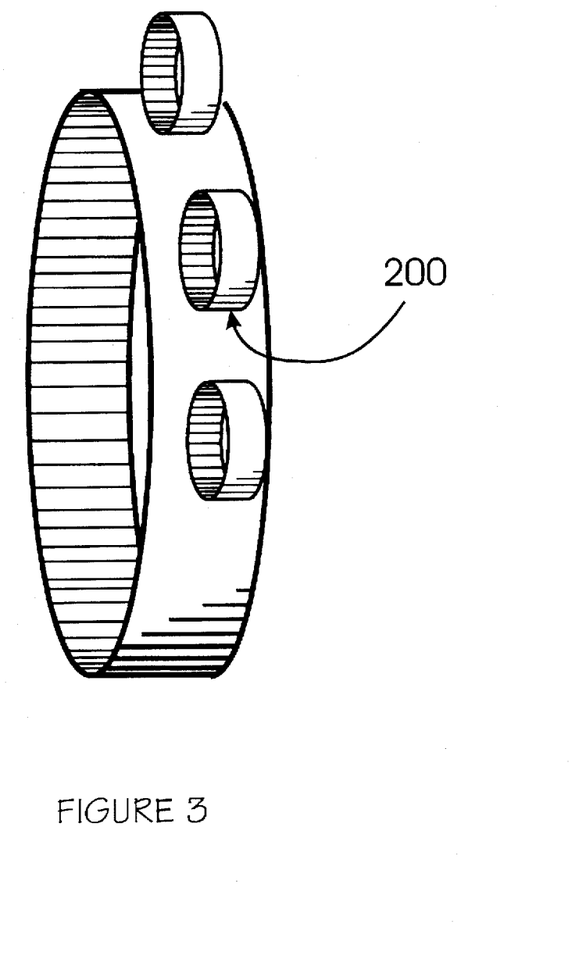
FIG. 3 is a perspective view of another preferred embodiment of the present invention including an integral connecting means and several clamps on a single strap.

FIG. 3 is a perspective view of another preferred embodiment of the present invention. Depicted in FIG. 3 is a connecting means 200 that is integral to the strap (and, consequently, the clamp), such as from "Velcro" or snaps and the like. As can be seen, the preferred embodiment of the integral connecting means 200 will permit the attachment of several clamps. This embodiment would be particularly useful in tending IV tubes and the like running to a hospital patient, where there is typically the need to tether several tubes and the like to a single patient. As with the strap 100, the materials of construction and the resistance to releasing of the connecting means 200 will depend upon the expected weight of the cable, etc. to be tethered; a heavy cable, etc. will include the restraining strength necessary to tend such a cable.

Figure 4:
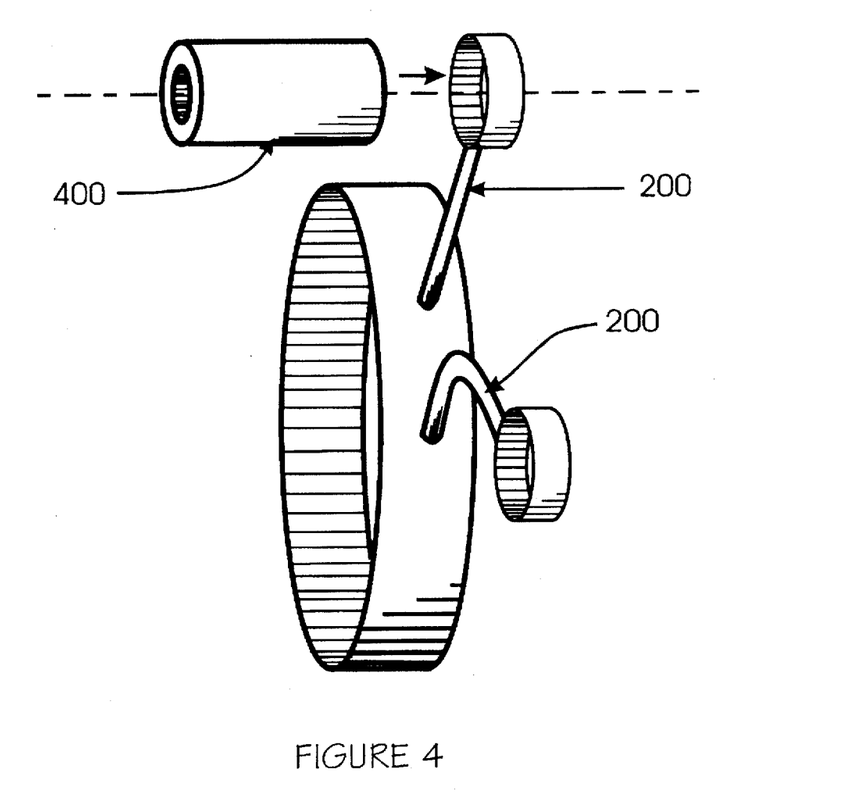
FIG. 4 is a perspective view of another preferred embodiment of the present invention showing both a rigid and a flexible elongated connecting means.

FIG. 4 is a perspective view of another preferred embodiment of the present invention showing both a rigid and a flexible connecting means 200. As also depicted by FIG. 4, the connecting means 200 can be elongated.

The clamp 300 is also depicted in a generic way in FIG. 2. In the preferred embodiment, the clamp 300 will be comprised of a flexible material, such as a type of cloth webbing or pliable plastic, that will wrap around or slip over a cable, tube, and the like. Just as for the strap 100, the clamp 300 could be constructed of a rigid or semi-rigid material such as plastic to provide a more rigid attachment to the cable, tube, and the like. Also, as with the strap 100, the clamp 300 could be provided in various colors and textures, depending upon the intended application.

Furthermore, in it's preferred form, the clamp 300 may also include a releasable closure means, such as "Velcro" or snaps, such that the user can automatically release himself from the tube, cord, or cable by pulling away from it (i.e. by exerting a force distal to the tube, etc.). As with the strap 100 and connecting means 200, the materials of construction and the resistance to releasing of the clamp 300 will depend upon the expected weight of the cable, etc. to be tethered; a heavy cable, etc. will include the strength necessary to exert a sufficiently large retaining force.

The clamp 300 may also be configured to accept a sheath over its entirety; the properties of the clamp sheath would typically be the same as those described above for the strap sheath.

The clamp 300 further may include a display portion for inscribing indicia thereon, such as the tube being tended by that particular clamp 300, or other indicia. The display portion could be configured to accept erasable or permanent inscriptions.

In its preferred embodiment, the clamp 300 will be configured to grip several different sizes of tube, cable and the like. One way of accomplishing this is with the clamp insert 400 depicted in FIG. 4. The clamp insert 400 might typically be utilized in concert with a clamp 300 constructed from a rigid or semi-rigid material. Another alternative for gripping different sized members would be to construct the clamp 300 of flexible material and include a closure means that adjusts for size, such as from "Velcro," for example. Additionally, the clamp 300 and/or clamp insert 400 could be sized to hold a writing implement.

Figure 5A:
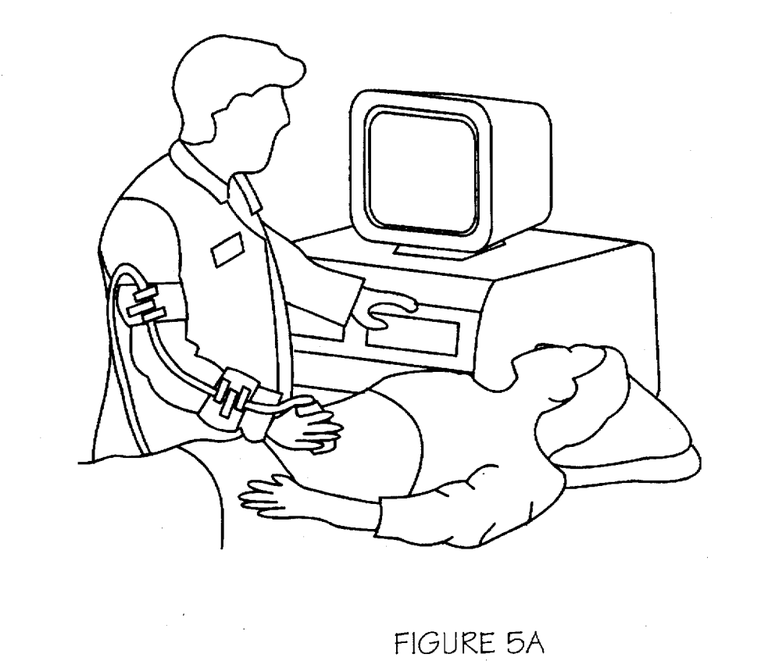
FIGS. 5a and 5b are depictions of preferred uses of the present invention.
Figure 5B:
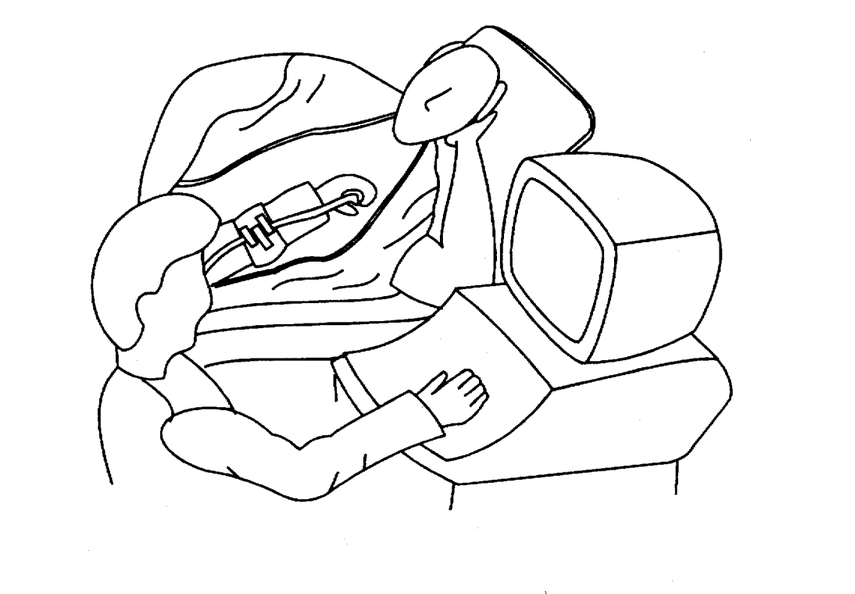

FIGS. 5a and 5b are depictions of preferred uses of the present invention. FIG. 5a depicts an operator of hospital ultrasound equipment (such as shown in FIGS. 1a–c) utilizing the present invention to tend the cable. FIG. 5b depicts a user of an electric hand tool (a hedge trimmer), utilizing the present invention.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A means for tethering elongated members to a human body comprising:

strap means for attaching the tether to an appendage of a human body by substantially encircling the appendage;

a plurality of clamps for releasably restraining elongated members; and a plurality of connecting means disposed on said strap means for connecting said strap means to each of said clamps, each one of said connecting means defining a fixed length, wherein at least two of said fixed lengths differ so that at least two of said clamps are located at differing radial distances from said strap means.

2. The tethering means recited in claim 1 wherein each of said connecting means is releasably attached to said strap means.

3. The tethering means recited in claim 2 wherein each of said connecting means is rigid.

4. The tethering means recited in claim 2 wherein each of said connecting means is flexible.

5. The tethering means recited in claim 1 wherein each of said clamps is configured to accept elongated members of various diameters.

6. The tethering means recited in claim 5 wherein each of said clamps further comprises a closure means that is releasably closed, whereby the elongated member will be released through application of distal force with relation to said strap.

7. The tethering means recited in claim 6 wherein each of said clamps further includes display means for inscribing indicia thereon.

8. The tethering means recited in claim 7 wherein each of said clamps further includes a disposable sheath disposed over substantially the entirety of each of said clamps to maintain each said clamp in a sanitary condition, and whereby said sheath can be removed and replaced.

9. The tethering means recited in claim 1 wherein said strap means further comprises a closure means that is releasably closed whereby said strap means will be released from the human body through application of a distal force with relation to the human body.

10. The tethering means recited in claim 9 wherein said strap means further includes display means for attaching indicia thereon.

11. The tethering means recited in claim 1, further comprising:

a first display surface disposed on said strap means whereon indicia can be inscribed;

a removable sheath slidingly attached over said strap means;

a second display surface disposed on at least one of said clamps whereon indicia can be inscribed; and a removable disposable sheath slidingly attached over substantially the entirety of each clamp to maintain said clamps in a sanitary condition.

12. The tethering means recited in claim 11, wherein:

said strap means further comprises a releasable closure means whereby said strap means will be released from the appendage through the application of a sufficiently large distal force with relation to the appendage; and each clamp further comprises a releasable closure means whereby the elongated member will be released from the clamp through the application of a sufficiently large distal force with relation to said clamp.

13. The tethering means recited in claim 12 wherein said connecting means is integral to said strap means.

14. The tethering means recited in claim 13 wherein said strap means, said connecting means and said clamps comprise a single piece of flexible material.

15. The tethering means recited in claim 14, further including at least one clamp insert for holding elongate members having smaller diameters than said clamps, each said clamp insert being insertible through one of said clamps.

* * * * *